(12) United States Patent
Inoue et al.

(10) Patent No.: US 12,427,220 B2
(45) Date of Patent: Sep. 30, 2025

(54) PERFUME HOLDING MEMBER AND FRAGRANCE PROVIDING DEVICE

(71) Applicant: Sony Group Corporation, Tokyo (JP)

(72) Inventors: Yukito Inoue, Tokyo (JP); Shuji Fujita, Tokyo (JP); Kazutaka Takaki, Kanagawa (JP)

(73) Assignee: Sony Group Corporation, Tokyo (JP)

( * ) Notice: Subject to any disclaimer, the term of this patent is extended or adjusted under 35 U.S.C. 154(b) by 371 days.

(21) Appl. No.: 17/920,562

(22) PCT Filed: Mar. 15, 2021

(86) PCT No.: PCT/JP2021/010263
§ 371 (c)(1),
(2) Date: Oct. 21, 2022

(87) PCT Pub. No.: WO2021/220643
PCT Pub. Date: Nov. 4, 2021

(65) Prior Publication Data
US 2023/0149585 A1    May 18, 2023

(30) Foreign Application Priority Data
Apr. 30, 2020 (JP) ................................. 2020-080675

(51) Int. Cl.
*A61L 9/12* (2006.01)
*B01F 23/23* (2022.01)
*B01F 23/231* (2022.01)

(52) U.S. Cl.
CPC ............ *A61L 9/12* (2013.01); *B01F 23/2312* (2022.01); *B01F 23/23121* (2022.01); *A61L 2209/15* (2013.01)

(58) Field of Classification Search
CPC . B01F 23/23; B01F 23/2312; B01F 23/23121
See application file for complete search history.

(56) References Cited

U.S. PATENT DOCUMENTS

2005/0006412 A1   1/2005   Albisetti et al.
2019/0026527 A1   1/2019   He
2019/0263527 A1   8/2019   Fantuzzi et al.

FOREIGN PATENT DOCUMENTS

GB        2401046 A  * 11/2004  ........... A61H 33/025
JP    H02-141516 U      11/1990
(Continued)

OTHER PUBLICATIONS

International Search Report and English translation thereof mailed Apr. 27, 2021 in connection with International Application No. PCT/JP2021/010263.
(Continued)

*Primary Examiner* — Robert A Hopkins
(74) *Attorney, Agent, or Firm* — Wolf, Greenfield & Sacks, P.C.

(57) ABSTRACT

A perfume holding member 101 includes: a perfume holder 208 that holds perfume; a holding space 209 where the perfume holder is disposed; a first opening 202 and a second opening 211 that open the holding space to the outside; movable portions 204 and 210 that move so as to open and close the first opening and the second opening; and a tolerance absorbing portion 207 that absorbs a tolerance between the first opening/closing position of the first opening of the movable portion and the second opening/closing position of the second opening of the movable portion. The holding space has an airflow passage including the first opening and the second opening, and the movable portions close the first opening and the second opening in a steady state and open the first opening and the second opening when the holding space is opened.

13 Claims, 10 Drawing Sheets

(56) References Cited

FOREIGN PATENT DOCUMENTS

| | | |
|---|---|---|
| JP | H05-23383 A | 2/1993 |
| JP | H11-348374 A | 12/1999 |
| JP | 2013-094436 A | 5/2013 |
| JP | 2014-000267 A | 1/2014 |
| JP | 2015-097695 A | 5/2015 |

OTHER PUBLICATIONS

PCT/JP2021/010263, Apr. 27, 2021, International Search Report.

* cited by examiner

PERFUME HOLDING MEMBER AND FRAGRANCE PROVIDING DEVICE

CROSS-REFERENCE TO RELATED APPLICATIONS

This application claims the benefit under 35 U.S.C. § 371 as a U.S. National Stage Entry of International Application No. PCT/JP2021/010263, filed in the Japanese Patent Office as a Receiving Office on Mar. 15, 2021, which claims priority to Japanese Patent Application Number JP2020-080675, filed in the Japanese Patent Office on Apr. 30, 2020, each of which is hereby incorporated by reference in its entirety.

TECHNICAL FIELD

The present technique relates to a perfume holding member and a fragrance providing device and more specifically relates to a perfume holding member and a fragrance providing device that provide a fragrance by opening and closing an air supply passage and a fragrance emission passage.

BACKGROUND ART

Conventionally, a technique is proposed to provide a fragrance for a user by supplying air into a storage device accommodating a perfume holding member that holds perfume, and emitting an air flow of vaporized perfume.

For example, PTL 1 proposes a fragrance providing device including; a shielding cylinder that is a cylinder having an internal cavity as a perfume-delivery air duct and an opening on a part of the side of the cylinder; a perfume container that accommodates perfume, is provided on the outer surface of the shielding cylinder, and has a side opening near the shielding cylinder; and blowing means capable of blowing air to one end of the perfume-delivery air duct, wherein the inside of the perfume container and the perfume-delivery air duct are allowed to communicate with each other by overlapping the opening of the shielding cylinder and the opening of the perfume container by relative rotations of the shielding cylinder and the perfume container in contact with each other, and the inside of the perfume container and the perfume-delivery air duct are prevented from communicating with each other by overlapping the opening of one of the shielding cylinder and the perfume container and a part other than the opening of one of the shielding cylinder and the perfume container by relative rotations of the shielding cylinder and the perfume container in contact with each other.

It is assumed that the fragrance providing device described in PTL 1 can suppress the emission of an unintended perfume and provide a fragrance with proper timing.

CITATION LIST

Patent Literature

PTL 1

JP 2013-094436 A

SUMMARY

Technical Problem

However, the fragrance providing device of PTL 1 may cause a leakage of perfume from a fitting portion between the perfume container and the case or an opening, for example, a fragrance inlet or outlet communicating with the outside. Thus, the perfume may be deteriorated (weakened by volatilization and altered by oxidization), mixed, or melt a label on the case or the like.

Hence, a main object of the present technique is to provide a perfume holding member and a fragrance providing device that can prevent a leakage of perfume from gaps such as a fitting portion and an opening.

Solution to Problem

The present technique provides a perfume holding member including: a perfume holder that holds perfume; a holding space where the perfume holder is disposed; a first opening and a second opening that open the holding space to the outside; movable portions that move so as to open and close the first opening and the second opening; and a tolerance absorbing portion that absorbs a tolerance between the first opening/closing position of the first opening of the movable portion and the second opening/closing position of the second opening of the movable portion. The holding space has an airflow passage including the first opening and the second opening, and the movable portions close the first opening and the second opening in a steady state and open the first opening and the second opening when the holding space is opened.

The movable portion may have an attached/detached portion that is attachable or detachable by a driving source and/or magnetic means.

The movable portion may have an elastic body urged in the closing direction of the first opening and the second opening.

The tolerance absorbing portion may have an elastic body that absorbs the tolerance.

The movable portion may have a first raised portion that closes the first opening and a second raised portion that closes the second opening.

The movable portion may be a linear-motion mechanism that linearly moves in the opening/closing direction of the first opening and the second opening.

The perfume holding member may further include a lock mechanism that closes the holding space in a steady state and opens the holding space upon attachment to an external device.

The perfume holding member may further include a first case that includes the holding space and the first opening and a second case that is attached to the first case and includes the second opening, and a sealing structure may be formed at a fitting portion between the first case and the second case.

The sealing structure may be an O ring.

The fitting portion between the first case and the second case may be made of an oil seal material and/or an elastic material.

The perfume holding member may have a surface composed of a material selected from the group consisting of resin with low gas permeability, an organic polymer, an organic low molecule, an organic metal, a metal, and a metal film, or a combination thereof.

The perfume holding member may have an inner wall made of a metal.

The perfume holding member may be a perfume cartridge attached to a fragrance providing device.

The present technique provides a fragrance providing device including a perfume holding member and a driving mechanism part, the perfume holding member including: a perfume holder that holds perfume; a holding space where the perfume holder is disposed, a first opening and a second opening that open the holding space to the outside; movable portions that move so as to open and close the first opening and the second opening, and a tolerance absorbing portion that absorbs a tolerance between the first opening/closing position of the first opening of the movable portion and the second opening/closing position of the second opening of the movable portion, the driving mechanism part being coupled to the movable portion and configured to drive the movable portion. The holding space has an airflow passage including the first opening and the second opening, and the movable portions close the first opening and the second opening in a steady state and open the first opening and the second opening when the holding space is opened.

Advantageous Effects of Invention

The present technique can prevent a leakage of perfume from gaps such as a fitting portion and an opening. The effect is not necessarily limited. Any effect described in the present specification or other effects achievable from the present specification may be obtained in addition to the foregoing effect or instead of the foregoing effect.

DESCRIPTION OF EMBODIMENTS

Figure 1:
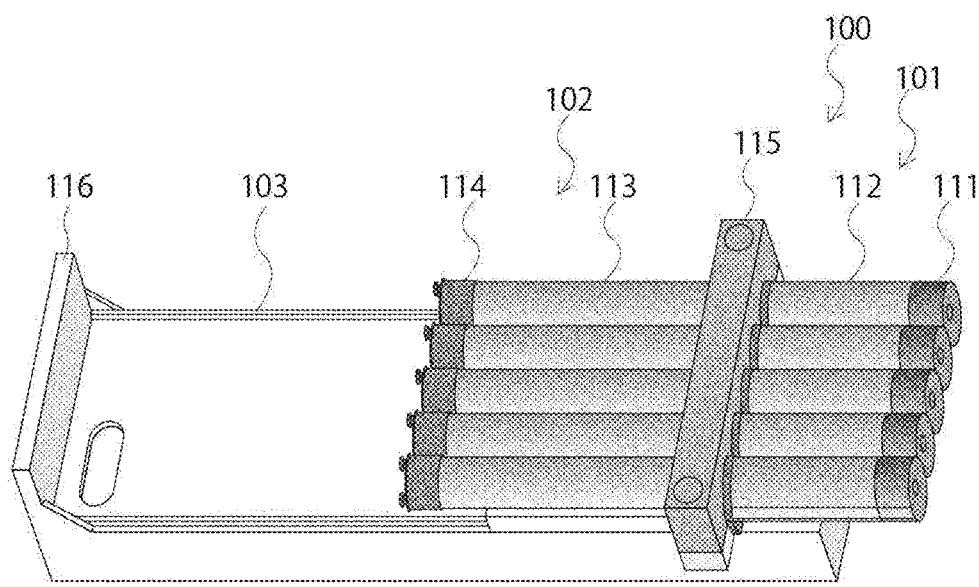
FIG. 1 is a perspective view illustrating a configuration example of a fragrance providing device according to a first embodiment of the present technique.
Figure 2:
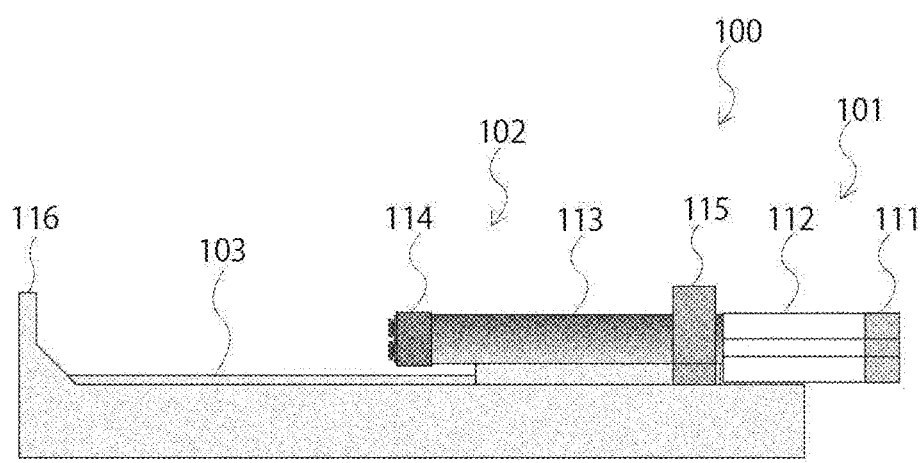
FIG. 2 is a side view illustrating the configuration example of the fragrance providing device according to the first embodiment of the present technique.
Figure 3:
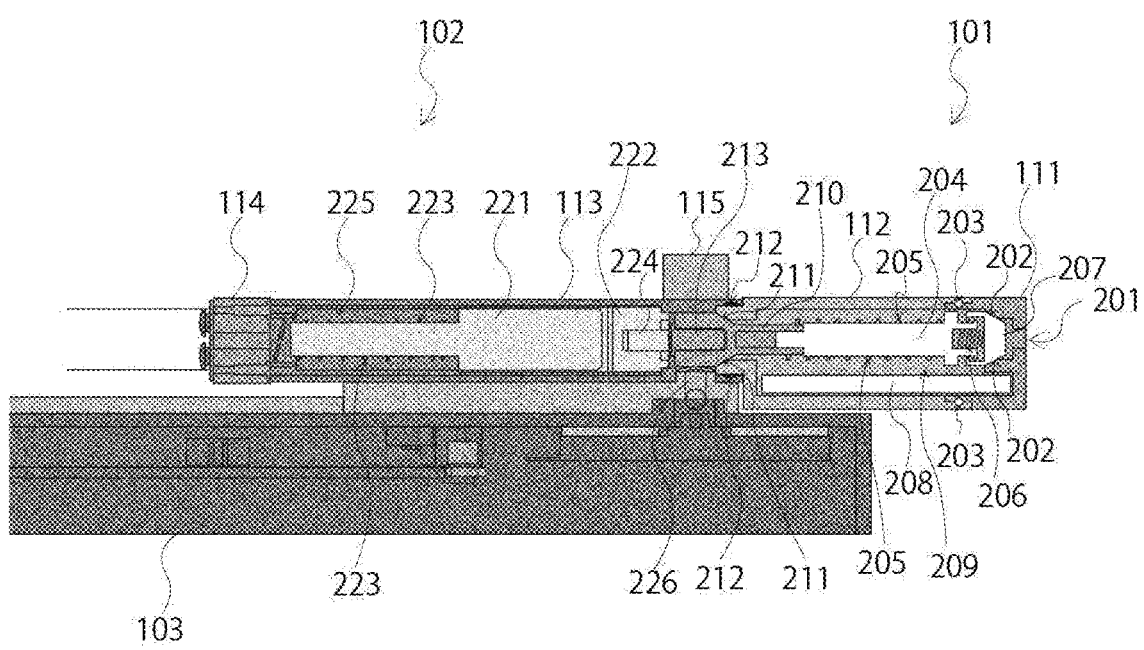
FIG. 3 is a side cross-sectional view illustrating the configuration example of the fragrance providing device according to the first embodiment of the present technique.
Figure 4:
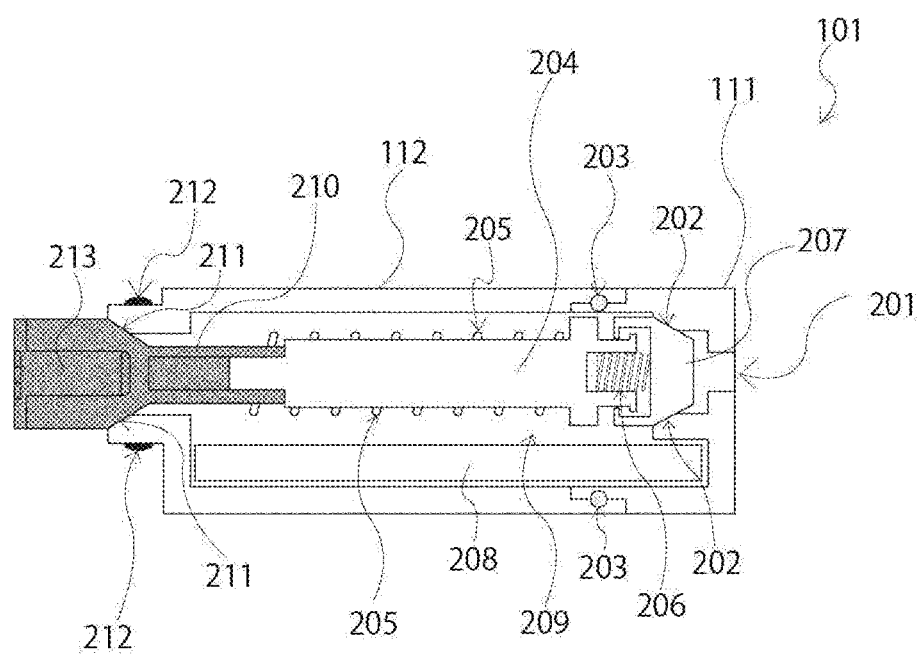
FIG. 4 is a side cross-sectional view illustrating a configuration example of a perfume holding member according to the first embodiment of the present technique.

Hereinafter, preferable embodiments for implementing the present technique will be described with reference to the drawings. The embodiments to be described hereinafter illustrate examples of typical embodiments of the present technique, and any of the embodiments can be combined. Moreover, the scope of the present technique should not be interpreted narrower by the embodiments. The description will proceed in the following order:

1. First Embodiment
(1) Configuration example of fragrance providing device
(1-1) Overall configuration
(1-2) Perfume cartridge (perfume holding member)
(1-3) Open/close mechanical part
(2) Operation example of fragrance providing device
(3) Modification example of perfume cartridge
(4) Modification example of coupling portion
2. Second Embodiment
(1) Configuration example of perfume cartridge
(2) Operation example of perfume cartridge 1. First Embodiment (1) Configuration Example of Fragrance Providing Device (1-1) Overall Configuration Referring to FIGS. 1 to 4, a configuration example of a fragrance providing device 100 according to a first embodiment of the present technique will be described below. FIG. 1 is a perspective view illustrating the configuration example of the fragrance providing device 100 according to the present embodiment. FIG. 2 is a side view illustrating the configuration example of the fragrance providing device 100. FIG. 3 is a side cross-sectional view illustrating the configuration example of the fragrance providing device 100. FIG. 4 is a side cross-sectional view illustrating a configuration example of a perfume cartridge (perfume holding member) 101 provided for the fragrance providing device 100.

As illustrated in FIGS. 1 and 2, the fragrance providing device 100 according to the present embodiment includes the cylindrical perfume cartridges 101 serving as the perfume holding members, cylindrical open/close mechanical parts 102, and a body part 103 substantially shaped like a rectangular solid. The perfume cartridge 101 includes a first case 111 and a second case 112 attached to the rear side of the first case 111. The open/close mechanical part 102 includes a sleeve case 113 and an open/close mechanical bottom 114 attached to the rear side of the sleeve case 113. The body part 103 includes an open/close mechanical fixing part 115 that fixes the open/close mechanical parts 102 and a stand 116 that restricts a rearward movement of the open/close mechanical parts 102.

In the fragrance providing device 100, the open/close mechanical parts 102 are placed on one end (front side) of the longitudinal direction of the top surface of the body part 103 and are fixed by the open/close mechanical fixing part 115. The stand 116 is provided on the other end (rear side) of the longitudinal direction of the top surface of the body part 103. The rear end of the second case 112 of the perfume cartridge 101 is detachably connected to the front side of the sleeve case 113 of the open/close mechanical part 102. The fragrance providing device 100 can be used in an upright position with the stand 116 placed at the bottom to direct the perfume cartridges 101 upward, so that a fragrance can be emitted upward.

As illustrated in FIG. 3, the fragrance providing device 100 passes air into a desired perfume holding space 209 selected from perfume holding spaces 209 provided in the respective perfume cartridges 101, and then vaporizes and emits perfume held by a perfume holder 208 disposed in the perfume holding space 209. For example, in the fragrance providing device 100, air supplied from an air pump, which is not illustrated, is passed into the perfume holding space 209 of the perfume cartridge 101, so that liquid perfume or moist perfume (hereinafter referred to as liquid perfume) is vaporized to emit a fragrance with air from the perfume holding space 209.

The fragrance providing device 100 is used as, for example, a device for emitting a fragrance into a space of a limited range. For example, a user feels relaxed by emitting a fragrance near the face of the user one or more times from the fragrance providing device 100. In this case, the fragrance providing device 100 emits a fragrance with high straightness and hardly diffuses the fragrance over a wide range, so that the fragrance is less likely to be sensed by persons around the user. The fragrance providing device 100 may be portable by the user or stationary.

(1-2) Perfume Cartridge

A configuration example of the perfume cartridge 101 will be described below, the perfume cartridge 101 serving as a perfume holding member provided for the fragrance providing device 100 according to the present embodiment.

As described above, the perfume cartridge 101 includes the first case 111 and the second case 112 attached to the rear side of the first case 111. The perfume cartridge 101 is cylindrical. The outside shape of the perfume holding member according to the present technique is not limited to a cylinder. For example, the perfume holding member can be formed into a circular column, a rectangular solid, a cube, or any other shape.

As illustrated in FIGS. 3 and 4, the first case 111 includes a discharge hole 201 that discharges perfumed air containing a perfume to the outside, a first opening 202 that discharges perfumed air, that is, a mixture of perfume and air into the discharge hole 201, and a first O ring 203 disposed at a fitting portion to the second case 112. The first opening 202 is formed with the front side tapered with a tilted face.

In the perfume cartridge 101, the first O ring 203 seals the fitting portion between the first case 111 and the second case 112, thereby preventing a leakage of perfume from the fitting portion. The first O ring 203 is not limited to this structure if the structure is an airtight sealing structure capable of sealing the fitting portion between the first case 111 and the second case 112. A fitting structure with a protrusion or a threaded structure may be used instead.

In the second case 112, the perfume holding space 209 is formed so as to hold liquid perfume with an airflow passage including the first opening 202 and a second opening 211. The first opening and the second opening can open the perfume holding space 209 to the outside. The perfume holding space 209 includes a shaft upper portion 204, a first spring 205 and a second spring 206 that are elastic bodies, a tolerance absorbing portion 207, the perfume holder 208 made of an impregnating material that holds liquid perfume, and a shaft lower portion 210.

The second case 112 includes the second opening 211 that feeds air from the outside into the perfume holding space 209 and a second O ring 212 that is disposed at a fitting portion to the open/close mechanical part 102. The second opening 211 is formed with the front side tapered with a tilted face. The shaft lower portion 210 has a portion attached to or detached from the open/close mechanical part 102, and the attached/detached portion has a metallic screw 213 that can be attached or detached by a driving source and/or magnetic means. The screw 213 is not limited to a metallic screw and may be any member attracted by a magnetic force.

The shaft upper portion 204 can move in the perfume holding space 209 in the extending direction and is urged by the first spring 205 in a direction that closes the first opening 202 on the front side. The shaft upper portion 204 is a movable portion that can move so as to open and close the first opening 202.

The tolerance absorbing portion 207 is connected to the front of the shaft upper portion 204 via the second spring 206. The tolerance absorbing portion 207 has a front portion tapered toward the front side. The face of the front portion of the tolerance absorbing portion 207 in a steady state is pressed to the face of the first opening 202 by an elastic force from the shaft upper portion 204, so that the first opening 202 is closed. Thus, the perfume cartridge 101 can prevent a leakage of perfume from the first opening 202 and the discharge hole 201.

As described above, the tolerance absorbing portion 207 has a structure acting as a cap that absorbs a tolerance at the sealing portion and closes the first opening 202. In this case, the tolerance means the manufacturing errors or variations of dimensions for sealing, for example, a distance between the first opening/closing position of the first opening 202 and the second opening/closing position of the second opening 211, an opening width, or the parallelism and length of a component. For example, even if parallelism is not obtained at the closed face, the tolerance absorbing portion 207 absorbs the inclination of the shaft upper portion 204 or the shaft lower portion 210 by the second spring 206, thereby keeping a closed state.

The first spring 205 is, for example, a coil spring but is not limited thereto. The first spring 205 may be an elastic body capable of urging the shaft upper portion 204 in the closing direction of the first opening 202. The second spring 206 is, for example, a coil spring but is not limited thereto. The second spring 206 may be an elastic body capable of absorbing a tolerance between the first opening/closing position of the first opening 202 and the second opening/closing position of the second opening 211 by means of the tolerance absorbing portion 207.

The shaft lower portion 210 is coupled to the rear of the shaft upper portion 204 and is movable with the shaft upper portion 204 in the perfume holding space 209 in the extending direction. The shaft lower portion 210 is a movable portion that can move so as to open and close the second opening 211, and is in contact with the second opening 211 in a steady state. The shaft upper portion 204 and the shaft lower portion 210 can be linear-motion mechanisms that linearly moves in the opening/closing direction of the first opening 202 and the second opening 211. The shaft lower portion 210 has a contact portion with the second opening 211 such that the contact portion is tapered toward the front side. The contact portion is pressed to the second opening 211 by the elastic force of the first spring 205 and closes the second opening 211 in a steady state. Thus, the perfume cartridge 101 can prevent a leakage of perfume from the second opening 211.

Furthermore, in the perfume cartridge 101, the second O ring 212 seals the fitting portion between the second case 112 and the open/close mechanical part 102, thereby preventing a leakage of perfume from the fitting portion. The first O ring 203 is not limited to this structure if the structure is an airtight sealing structure capable of sealing the fitting portion between the second case 112 and the open/close mechanical part 102. A threaded structure or the like may be used instead.

The perfume holder 208 holds liquid perfume. The perfume holder 208 shaped like a plate may have a cylindrical shape surrounding the side of the shaft upper portion 204. The liquid perfume may be, for example, essential oil or essential oil diluted with ethanol. The perfume holding space 209 has the function of passing air supplied from an air pump (not illustrated), which is an example of an air source. The second case 112 may include one or more perfume holding spaces 209.

Liquid perfume is deposited and held in a wet condition on at least a part of the inner surface of the perfume holding space 209. For example, after liquid perfume is fed into the perfume holding space 209, high-pressure gas such as air is supplied into the perfume holding space 209 for a predetermined time, so that the perfume can be deposited in a wet condition on the inner surface of the perfume holding space 209 while excessive liquid perfume is discharged out of the space.

The perfume cartridges 101 are coupled to one another on the body part 103, so that the fragrance providing device 100 can control the emission of a plurality of perfumes. In this case, the perfume cartridges 101 to receive supplied air can be switched by operating any one of the open/close mechanical parts 102 connected to the perfume cartridges 101. The perfume holding spaces 209 in the perfume cartridges 101 may hold the same liquid perfume or some or all of the perfume holding spaces 209 may hold different liquid perfumes. If the perfume holding spaces 209 hold different liquid perfumes, a fragrance to be emitted can be changed by switching the perfume cartridges 101 that can receive air supply.

The first case 111 and the second case 112 of the perfume cartridge 101 can be made of an organic polymeric material so as to increase the wetting of liquid perfume. Such an organic polymeric material may be, for example, any one of polyvinyl chloride, polyethylene, phenol resin, olefin resin, nylon, polyester, synthetic rubber, silicon resin, natural rubber, protein, nucleic acid, lipid, and polysaccharide or a mixture thereof. The first case 111 and the second case 112 are not limited to these examples. For example, the cases may be made of polymer resins such as acrylic resin, urethane resin, ABS resin, polyether ether ketone (PEEK) resin, polyacetal (POM) resin, fluorocarbon resin, cycloolefin polymer resin, and polyimide resin or one or two or more materials selected from metals such as stainless steel and aluminum, inorganic crystals such as quartz, or glass.

The second case 112 may include a reading unit capable of reading the contents of the perfume cartridge 101. The reading unit is not illustrated. For example, the surface of the second case 112 may have a label or a bar code.

The perfume cartridges 101 can be manufactured by using, for example, a 3D printer. In this case, a material suitable for a 3D printer may be selected as a material of the perfume cartridges 101.

(1-3) Open/Close Mechanical Part

A configuration example of the open/close mechanical part 102 provided for the fragrance providing device 100 according to the present embodiment will be described below.

As described above, the open/close mechanical part 102 includes the sleeve case 113 and the open/close mechanical bottom 114 attached to the rear side of the sleeve case 113. The open/close mechanical part 102 is coupled to the shaft upper portion 204 and the shaft lower portion 210, which are movable portions, and acts as a driving mechanism part for driving these portions. The open/close mechanical part 102 is cylindrical. The outside shape of the open/close mechanical part according to the present technique is not limited to a cylinder. For example, the open/close mechanical part can be formed into a circular column, a rectangular solid, a cube, or any other shape according to the perfume holding member.

As illustrated in FIG. 3, the sleeve case 113 has an operation space 225 in which an operation sleeve 221 can operate. The operation space 225 includes the operation sleeve 221, a magnet fixing portion 222, a bias spring 223, and a magnet 224. Moreover, an air intake 226 for taking in air or the like from the outside is formed on the lower portion of the front side of the sleeve case 113.

The operation sleeve 221 can be operated in the operation space 225 in the extending direction by the bias spring 223. The magnet fixing portion 222 is coupled to the front side of the operation sleeve 221, and the magnet 224 is fixed by the magnet fixing portion 222. When the front side of the sleeve case 113 and the rear side of the second case 112 of the perfume cartridge 101 are coupled to each other, the magnet 224 attracts the screw 213 with a magnetic force and comes into contact with the screw 213. In this way, in the perfume cartridge 101, magnet chucking on the portion attached to or detached from the open/close mechanical part 102 facilitates attachment and detachment to and from the open/close mechanical part 102. The attached or detached portion may be a valve coupling. Furthermore, linear-motion power from the open/close mechanical part 102 can be transmitted to the perfume cartridge 101. This eliminates the need for the provision of a driving source for the perfume cartridge 101.

The bias spring 223 is connected to the open/close mechanical bottom 114 having one end connected to the rear of the operation sleeve 221 and the other end attached to the rear side of the sleeve case 113. The open/close mechanical part 102 can operate the operation sleeve 221 rearward by means of an actuator acting as a driving source that is not illustrated, and returns the operation sleeve 221 forward to the original position by a restoring force of the bias spring 223 having been compressed at the time of the rearward operation. The bias spring 223 is, for example, a coil spring but is not limited thereto. The bias spring 223 may be an elastic body capable of operating operation sleeve 221 forward and rearward.

The actuator may be, for example, a linear-motion mechanism that linearly moves the operation sleeve 221 and includes a shape memory alloy, a motor, a solenoid, a linear-sliding type, or a small electromagnet. In this case, for the linear-motion mechanism, linear movements of some of a plurality of coupled members are included in addition to a linear movement of a single member.

(2) Operation Example of Fragrance Providing Device

Figure 5:
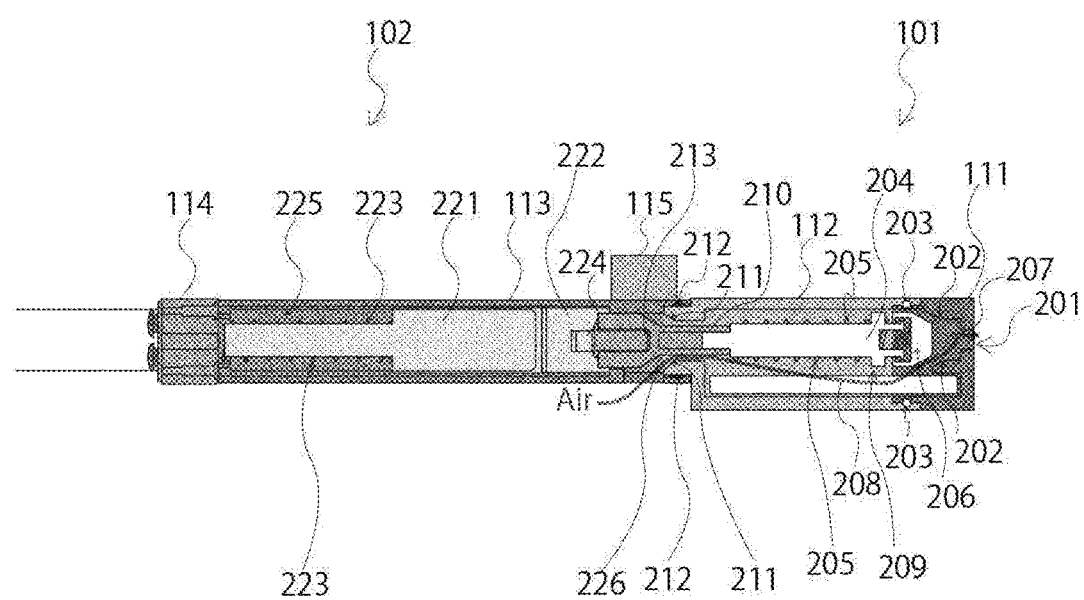
FIG. 5 is a side cross-sectional view illustrating an operation example of the fragrance providing device according to the first embodiment of the present technique.

Referring to FIG. 5, an example of an operation for emitting perfumed air from the fragrance providing device 100 will be described below. FIG. 5 is a side cross-sectional view illustrating the operation example of the fragrance providing device 100.

First, an air pump (not illustrated) coupled to the air intake 226 of the sleeve case 113 to supply air is turned on to feed air into the air intake 226 from the air pump. The air pump is an aspect of an air source. The air pump is driven by power supplied from a primary battery or a secondary battery and introduces air into an airflow passage. The air pump may be, for example, a diaphragm pump that deforms a diaphragm by supplying alternating current to a piezoelectric element and performs sucking and pumping of air.

Subsequently, the actuator coupled to the operation sleeve 221 is operated to linearly move the operation sleeve 221 to the rear side of the fragrance providing device 100. At this point, the bias spring 223 is pressed and compressed rearward from the operation sleeve 221.

Thus, the magnet 224 attached to the front of the operation sleeve 221 attracts the screw 213 rearward, so that the shaft lower portion 210 and the shaft upper portion 204 that are coupled to the screw 213 are moved rearward at the same time. At this point, the first spring 205 is pressed and compressed rearward from the shaft upper portion 204.

When the shaft upper portion 204 and the shaft lower portion 210 move rearward, the first opening 202 and the second opening 211 that have been closed by the shaft upper portion 204 and the shaft lower portion 210 are simultaneously opened, so that the perfume holding space 209 is opened to the outside. When the second opening 211 is opened, air fed into the air intake 226 flows into the perfume holding space 209 from the second opening 211.

Thereafter, air flowing into the perfume holding space 209 and perfumed air that contains air and a perfume contained in the perfume holder 208 in the perfume holding space 209 are emitted through the first opening 202 to a user outside the discharge hole 201.

When the power of the actuator is turned off after the perfumed air is emitted, the operation sleeve 221 is returned to the original position in a steady state by a restoring force of the bias spring 223. The shaft upper portion 204 and the shaft lower portion 210 are slid forward into contact with the first opening 202 and the second opening 211 by a restoring force of the first spring 205. The first opening 202 and the second opening 211 are closed in a steady state by a sliding capping mechanism including the shaft upper portion 204 and the shaft lower portion 210. At this point, even if a tolerance occurs, the first opening 202 and the second opening 211 can be opened at the same time by the tolerance absorbing portion 207.

By adjusting the forces and displacements of the first spring 205, the second spring 206, the bias spring 223, and the actuator, the fragrance providing device 100 can adjust an amount of tolerance absorption by the tolerance absorbing portion 207.

The fragrance providing device 100 simultaneously opens and closes the first opening 202 and the second opening 211 to improve responsiveness. In order to improve the power of discharge from the discharge hole 201, the mechanism may open and close the openings with a time difference. For example, the first opening 202 may be opened after the second opening 211 is opened.

According to the related art, perfume steadily leaks from the fitting portion between the first case 111 and the second case 112, the fitting portion between the second case 112 and the open/close mechanical part 102, the first opening 202, and the second opening 211. Thus, the perfume may be deteriorated (weakened by volatilization and altered by oxidization), mixed, or melt a label. Because of this problem, a perfume cartridge in the related art is not suitable for long storage and thus is sealed with an aluminum pouch to prevent deterioration of the perfume.

In contrast, the fragrance providing device 100 provided with the perfume cartridges 101 according to the present embodiment steadily closes the fitting portion between the first case 111 and the second case 112, the fitting portion between the second case 112 and the open/close mechanical part 102, the first opening 202, and the second opening 211, thereby preventing a leakage of perfume from these gaps.

Since the perfume holding space 209 of the perfume cartridge 101 can be closed until a certain pressure is received, the valve of an air-supply passage portion can be opened after the pump or the like is turned on. Thus, the fragrance providing device 100 keeps air intake and exhaust in one direction, thereby preventing a back flow, protecting the device, and preventing contamination (mixing of perfume).

Moreover, the tolerance absorbing structure of the tolerance absorbing portion 207 can structurally control whether to first open the second opening 211 serving as an air supply passage or the first opening 202 serving as an emission passage of perfumed air. Thus, the fragrance providing device 100 opens the first opening 202 after opening the second opening 211 or closes the first opening 202 after closing the second opening 211, thereby preventing a back flow, protecting the device, and preventing contamination.

In order to prevent the permeation of gas in the perfume cartridge 101, the fitting portion between the first case 111 and the second case 112 can be coated with an oil seal material or an elastic material such as silicone rubber or fluorocarbon rubber or can be made of an oil seal material and an elastic material in combination. For the same purpose, the surface of the perfume cartridge 101 can be composed of a material selected from fluorocarbon resin with low gas permeability, an organic polymeric or organic low-molecular assembly, e.g., a polymer membrane, a SAM, or an LB film, an organic metal, a metal, and a metal film, or a combination thereof. The metal or the metal film can be used for metallization. Furthermore, the inner wall surface of the perfume cartridge 101 can be made of a metal.

(3) Modification Example of Perfume Cartridge

Figure 6:
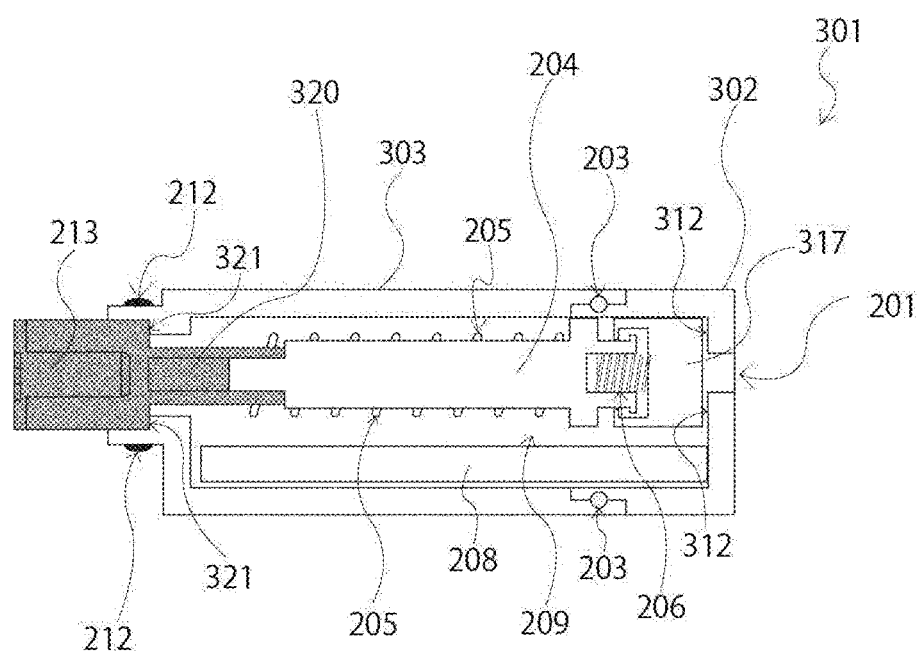
FIG. 6 is a side cross-sectional view illustrating a modification example of the perfume holding member according to the first embodiment of the present technique.

Referring to FIG. 6, a modification example of the perfume cartridge 101 will be described below. FIG. 6 is a side cross-sectional view illustrating the modification example of the perfume cartridge 101 according to the present embodiment. A perfume cartridge 301 of the present modification example is different from the perfume cartridge 101 in that a contact surface between an opening and a shaft portion is not inclined and the opening and the shaft portion are formed on surfaces perpendicular to the moving direction of the shaft portion. Other configurations of the perfume cartridge 301 are identical to those of the perfume cartridge 101. The same configurations are indicated by the same reference numerals.

As illustrated in FIG. 6, the perfume cartridge 301 includes a first case 302 and a second case 303 attached to the rear side of the first case 302. The perfume cartridge 301 is cylindrical. The outside shape of the perfume holding member according to the present technique is not limited to a cylinder. For example, the perfume holding member can be formed into a circular column, a rectangular solid, a cube, or any other shape.

The first case 302 includes the discharge hole 201 that discharges perfumed air containing a perfume to the outside, a first opening 312 that discharges perfumed air, that is, a mixture of perfume and air into the discharge hole 201, and the first O ring 203 disposed at a fitting portion to the second case 303. The first opening 312 has a contact surface with the shaft upper portion 204 such that the contact surface is perpendicular to the moving direction of the shaft upper portion 204. In the perfume cartridge 301, the first O ring 203 seals the fitting portion between the first case 302 and the second case 303, thereby preventing a leakage of perfume from the fitting portion.

In the second case 303, the perfume holding space 209 that holds liquid perfume is formed. The perfume holding space 209 includes the shaft upper portion 204, the first spring 205, the second spring 206, a tolerance absorbing portion 317, the perfume holder 208, and a shaft lower portion 320.

The second case 303 includes a second opening 321 that feeds air from the outside into the perfume holding space 209 and the second O ring 212 that is disposed at a fitting portion to the open/close mechanical part 102. The second opening 211 has a contact surface with the shaft lower portion 320 such that the contact surface is perpendicular to the moving direction of the shaft lower portion 320. The metallic screw 213 is provided at the contact portion of the shaft lower portion 210 with the open/close mechanical part 102.

The shaft upper portion 204 can move in the perfume holding space 209 in the extending direction and is urged by the first spring 205 toward the first opening 202 on the front side.

The tolerance absorbing portion 317 is connected to the front of the shaft upper portion 204 via the second spring 206. The tolerance absorbing portion 317 has a front portion with a face perpendicular to the moving direction of the shaft upper portion 204. The face of the front portion of the tolerance absorbing portion 317 in a steady state is pressed to the face of the first opening 312 by an elastic force from the shaft upper portion 204, so that the first opening 312 is closed. Like the tolerance absorbing portion 207, the tolerance absorbing portion 317 has a structure acting as a cap that absorbs a tolerance at the sealing portion and closes the first opening 312. Thus, the perfume cartridge 301 can prevent a leakage of perfume from the first opening 312 and the discharge hole 201.

The first spring 205 may be an elastic body capable of urging the shaft upper portion 204 in the closing direction of the first opening 312. The second spring 206 may be an elastic body capable of absorbing a tolerance between the first opening/closing position of the first opening 312 and the second opening/closing position of the second opening 321 by means of the tolerance absorbing portion 317.

The shaft lower portion 320 is coupled to the rear of the shaft upper portion 204 and is movable with the shaft upper portion 204 in the perfume holding space 209 in the extending direction. The shaft lower portion 320 is in contact with the second opening 321 in a steady state. The shaft lower portion 320 has a contact portion with the second opening 321 such that the contact portion is formed with a face perpendicular to the moving direction of the shaft lower portion 320. The contact portion is pressed to the second opening 321 by an elastic force of the first spring 205, so that the second opening 321 is closed in a steady state. Thus, the perfume cartridge 301 can prevent a leakage of perfume from the second opening 321.

Furthermore, in the perfume cartridge 301, the second O ring 212 seals the fitting portion between the second case 303 and the open/close mechanical part 102, thereby preventing a leakage of perfume from the fitting portion.

The perfume cartridge 301 provided for the fragrance providing device according to the present technique can achieve the same effect as the fragrance providing device 100. Moreover, in the perfume cartridge 301, the contact surfaces between the first opening 312 and the second opening 321 and the shaft upper portion 204 and the shaft lower portion 320 are perpendicular to the moving directions of the shaft upper portion 204 and the shaft lower portion 320, so that the perfume cartridge 301 can be manufactured with greater ease than the perfume cartridge 101. The perfume cartridge 301 can increase the airtightness of the contact surfaces with greater ease than the perfume cartridge 101, thereby preventing a leakage of perfume with higher accuracy.

(4) Modification Example of Coupling Portion

Figure 7:
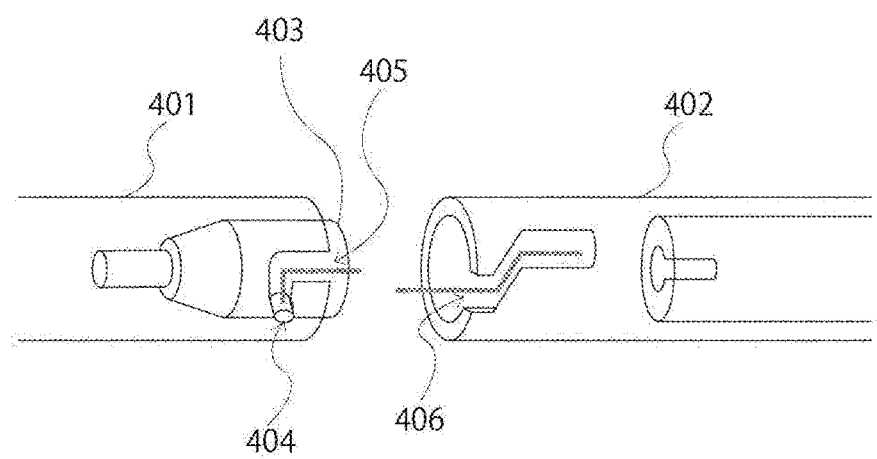
FIG. 7 is a side perspective view illustrating a modification example of a coupling portion between the perfume holding member and an open/close mechanical part according to the first embodiment of the present technique.

Referring to FIG. 7, a modification example of the fragrance providing device 100 will be described below. FIG. 7 is a side perspective view illustrating a modification example of a coupling portion between the perfume cartridge 101 and the open/close mechanical part 102. A coupling portion between a perfume cartridge 401 and an open/close mechanical part 402 of the present modification example has a lock mechanism. Other configurations are identical to those of the perfume cartridge 101 and the open/close mechanical part 102, and thus an explanation thereof is omitted.

As illustrated in FIG. 7, the perfume cartridge 401 has a sealing portion 403 attached to the rear end coupled to the open/close mechanical part 402. On the sealing portion 403, a protruding portion 404 is formed. On the rear end of the perfume cartridge 401, an L-shaped protrusion fixing groove 405 is formed so as to receive the inserted protruding portion 404. When the sealing portion 403 is attached to the perfume cartridge 401, the protruding portion 404 is inserted into the protrusion fixing groove 405, and then the sealing portion 403 is rotated in the circumferential direction of the cross section of the perfume cartridge 401 such that the sealing portion 403 is fixed with the protruding portion 404 held by the bending portion of the protrusion fixing groove 405.

The open/close mechanical part 402 has a protrusion moving groove 406 at the front to be coupled to the perfume cartridge 401, the protrusion moving groove 406 including a linear portion, a tilted portion, and a linear portion where the protruding portion 404 can be inserted.

When the perfume cartridge 401 is attached to the open/close mechanical part 402, first, the rear of the perfume cartridge 401 and the front of the open/close mechanical part 402 are coupled to each other while aligning the openings of the protrusion fixing groove 405 and the protrusion moving groove 406. The sealing portion 403 is then rotated opposite to the direction of fixing the protruding portion 404 into the protrusion fixing groove 405, so that the protruding portion 404 is released from the protrusion fixing groove 405. The protruding portion 404 is then slid from the protrusion fixing groove 405 according to the shape of the protrusion moving groove 406. Thus, the sealing portion 403 moves into the open/close mechanical part 402 during the attachment, and the inside of the perfume cartridge 401 and the inside of the open/close mechanical part 402 communicate with each other so as to open the perfume holding space.

When the perfume cartridge 401 alone is placed in a steady state, the lock mechanism of the coupling portion between the perfume cartridge 401 and the open/close mechanical part 402 closes the perfume holding space so as to prevent a leakage of perfume from the rear end of the perfume cartridge 401 and prevent a lid or the like on the rear end from being accidentally removed to cause a leakage of perfume. Moreover, the perfume cartridge 401 and the open/close mechanical part 402 can be coupled to each other in a sealing state and thus prevent a leakage of perfume even after the coupling.

2. Second Embodiment

(1) Configuration Example of Perfume Cartridge

Figure 8:
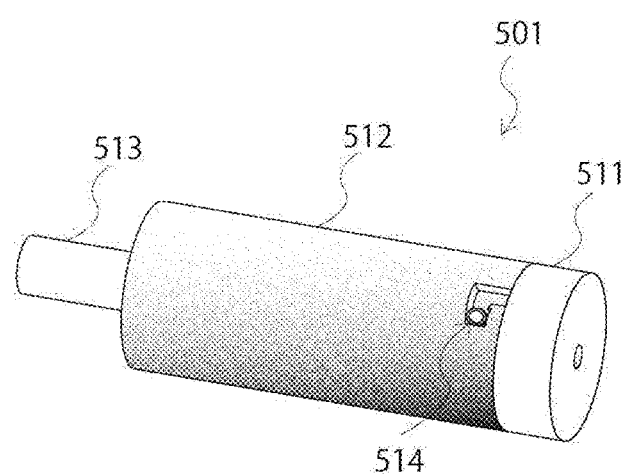
FIG. 8 is a perspective view illustrating a configuration example of a perfume holding member according to a second embodiment of the present technique.
Figure 9:
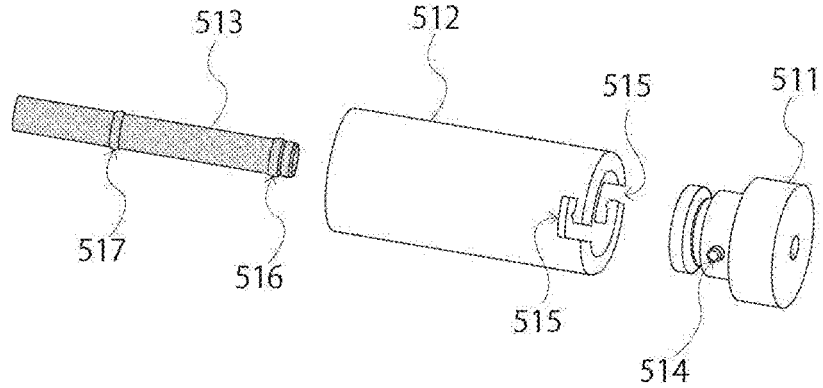
FIG. 9 is an exploded perspective view illustrating the configuration example of the perfume holding member according to the second embodiment of the present technique.
Figure 10:
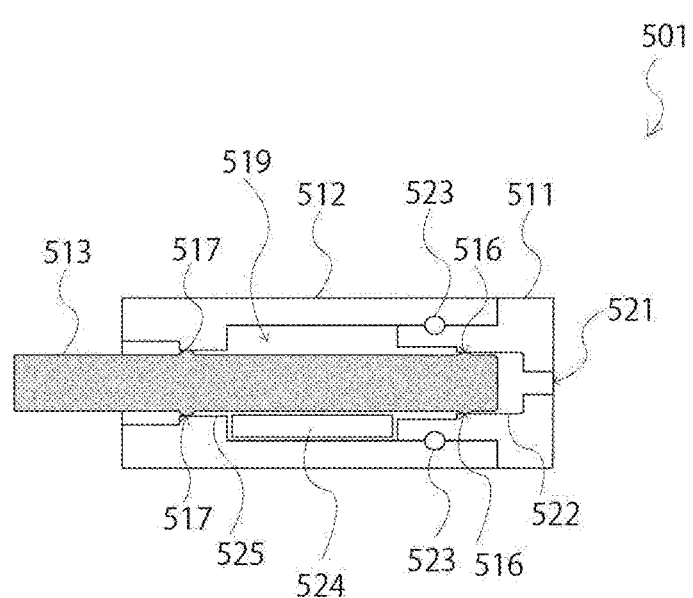
FIG. 10 is a side cross-sectional view illustrating the configuration example of the perfume holding member according to the second embodiment of the present technique.

Referring to FIGS. 8 to 10, a configuration example of a perfume cartridge 501 according to a second embodiment of the present technique will be described below. FIG. 8 is a perspective view illustrating the configuration example of the perfume cartridge 501 according to the present embodiment. FIG. 9 is an exploded perspective view illustrating the configuration example of the perfume cartridge 501. FIG. 10 is a side cross-sectional view illustrating the configuration example of the perfume cartridge 501. The perfume cartridge 501 is different from the perfume cartridge 101 according to the first embodiment in that the inner surfaces of openings and the raised portions of a shaft portion are brought into contact with each other to form a sealing structure.

As illustrated in FIGS. 8 and 9, the perfume cartridge 501 according to the present embodiment is cylindrical and includes a first case 511, a second case 512 attached to the rear side of the first case 511, and a shaft portion 513 that is movable in the first case 511 and the second case 512 in the extending direction. However, the shape of the perfume cartridge 501 is not limited to a cylinder.

The first case 511 has two protruding portions 514 opposed to each other on the side of a coupling portion to the second case 512. The second case 512 has two L-shaped protrusion fixing grooves 515, in which the protruding portions 514 can be inserted, on a coupling portion to the first case 511. The number of protruding portions 514 and the number of protrusion fixing grooves 515 are not limited to two and may be one or three or more.

When the first case 511 and the second case 512 are coupled to each other, the protruding portions 514 are inserted into the protrusion fixing grooves 515, and then the first case 511 is rotated in the circumferential direction of the cross section of the perfume cartridge 501 such that the first case 511 is fixed with the protruding portions 514 held by the bending portions of the protrusion fixing grooves 515.

As illustrated in FIG. 9, the shaft portion 513 is cylindrical and has a first raised portion 516 and a second raised portion 517 at spaced points on the side of the shaft portion 513. The first raised portion 516 and the second raised portion 517 are circular in cross section perpendicularly to the axial direction. A distance between the first raised portion 516 and the second raised portion 517 corresponds to a distance between the circumferential portion of a first opening 522 and the circumferential portion of a second opening 525. The first opening 522 and the second opening 525 will be described later.

As illustrated in FIG. 10, the first case 511 includes a discharge hole 521 that discharges perfumed air containing a perfume to the outside, the first opening 522 that feeds perfumed air, that is, a mixture of perfume and air into the discharge hole 521, and a first O ring 523 disposed at a fitting portion to the second case 512.

In the perfume cartridge 501, the first O ring 523 seals the fitting portion between the first case 511 and the second case 512, thereby preventing a leakage of perfume from the fitting portion.

In the second case 512, a perfume holding space 519 that holds liquid perfume is formed. The perfume holding space 519 includes the shaft portion 513 and a perfume holder 524. The perfume holder 524 shaped like a plate may have a cylindrical shape surrounding the side of the shaft portion 513. The second case 512 includes the second opening 525 that feeds air from the outside into the perfume holding space 519. The shaft portion 513 is a movable portion that can move so as to open and close the first opening 522 and the second opening 525 at the same time or with a time difference.

The diameters of the first opening 522 and the second opening 525 are smaller than the internal space of the perfume holding space 519 or the like and are substantially equal to the diameters of the cross sections of the first raised portion 516 and the second raised portion 517 perpendicularly to the axial direction. Thus, when the shaft portion 513 is stored in the first case 511 and the second case 512, the first raised portion 516 and the second raised portion 517 come into contact with the inner surfaces of the first opening 522 and the second opening 525, thereby closing the first opening 522 and the second opening 525.

The circumferential portion of the first opening 522 and the circumferential portion of the second opening 525 have large widths in the extending direction. The widths of the circumferential portions act as tolerance absorbing structures for absorbing tolerances. The first opening 522 and the second opening 525 can be opened and closed at the same time or with a time difference by adjusting the widths of the circumferential portions acting as the tolerance absorbing structures.

(2) Operation Example of Perfume Cartridge

Referring to FIG. 10, an example of an operation for emitting perfumed air from the perfume cartridge 501 will be described below.

When the shaft portion 513 is moved to the rear side of the perfume cartridge 501 by a driving force of an actuator or the like, the first raised portion 516 and the second raised portion 517 are separated from the inner surfaces of the first opening 522 and the second opening 525, thereby opening the first opening 522 and the second opening 525. At this point, the first opening 522 and the second opening 525 can be opened at the same time or with a time difference by adjusting the widths of the circumferential portions of the first opening 522 and the second opening 525 in the extending direction.

When the second opening 525 is opened, air fed into an air intake flows into the perfume holding space 519 of the second case 512 from the second opening 525.

Thereafter, air flowing into the perfume holding space 519 and perfumed air that contains air and a perfume contained in the perfume holder 524 in the perfume holding space 519 are emitted through the first opening 522 to a user outside the discharge hole 521.

After the emission of the perfumed air, the shaft portion 513 is slid to the original position to bring the first raised portion 516 and the second raised portion 517 into contact with the inner surfaces of the circumferential portions of the first opening 522 and the second opening 525, so that the first opening 522 and the second opening 525 are closed. At this point, by adjusting the widths of the circumferential portions of the first opening 522 and the second opening 525 in the extending direction, the first opening 522 and the second opening 525 can be closed at the same time regardless of the tolerances of the first raised portion 516 and the second raised portion 517 in the extending direction even if a tolerance occurs between the first opening 522 and the second opening 525.

With this configuration, in addition to the same effect as the first embodiment, the perfume cartridge 501 according to the present embodiment can absorb a tolerance between the circumferential portions of the first opening 522 and the second opening 525 and easily control the opening/closing of the openings regardless of the tolerances of the first raised portion 516 and the second raised portion 517 in the extending direction.

The present technique can be configured as follows:

(1) A perfume holding member including:
a perfume holder that holds perfume;
a holding space where the perfume holder is disposed;
a first opening and a second opening that open the holding space to outside;
movable portions that move so as to open and close the first opening and the second opening; and
a tolerance absorbing portion that absorbs a tolerance between a first opening/closing position of the first opening of the movable portion and a second opening/closing position of the second opening of the movable portion, wherein the holding space has an airflow passage including the first opening and the second opening, and
the movable portions close the first opening and the second opening in a steady state and open the first opening and the second opening when the holding space is opened.

(2) The perfume holding member according to (1), wherein the movable portion has an attached/detached portion that is attachable or detachable by a driving source and/or magnetic means.

(3) The perfume holding member according to (1) or (2), wherein the movable portion has an elastic body urged in a closing direction of the first opening and the second opening.

(4) The perfume holding member according to any one of (1) to (3), wherein the tolerance absorbing portion has an elastic body that absorbs the tolerance.

(5) The perfume holding member according to (1) or (2), wherein the movable portion has a first raised portion that closes the first opening and a second raised portion that closes the second opening.

(6) The perfume holding member according to any one of (1) to (5), wherein the movable portion is a linear-motion mechanism that linearly moves in an opening/closing direction of the first opening and the second opening.

(7) The perfume holding member according to any one of (1) to (6), further including a lock mechanism that closes the holding space in a steady state and opens the holding space upon attachment to an external device.

(8) The perfume holding member according to any one of (1) to (7), further including a first case that includes the holding space and the first opening and a second case that is attached to the first case and includes the second opening, and
wherein a sealing structure is formed at a fitting portion between the first case and the second case.

(9) The perfume holding member according to (8), wherein the sealing structure is an O ring.

(10) The perfume holding member according to (8) or (9), wherein the fitting portion between the first case and the second case is made of an oil seal material and/or an elastic material.

(11) The perfume holding member according to any one of (1) to (10), wherein the perfume holding member has a surface composed of a material selected from the group consisting of resin with low gas permeability, an organic polymer, an organic low molecule, an organic metal, a metal, and a metal film, or a combination thereof.

(12) The perfume holding member according to any one of (1) to (11), wherein the perfume holding member has an inner wall made of a metal.

(13) The perfume holding member according to any one of (1) to (12), wherein the perfume holding member is a perfume cartridge attached to a fragrance providing device.

(14) A fragrance providing device comprising a perfume holding member and a driving mechanism part,
the perfume holding member including:
a perfume holder that holds perfume;
a holding space where the perfume holder is disposed;
a first opening and a second opening that open the holding space to outside;
movable portions that move so as to open and close the first opening and the second opening; and
a tolerance absorbing portion that absorbs a tolerance between a first opening/closing position of the first opening of the movable portion and a second opening/closing position of the second opening of the movable portion, the driving mechanism part being coupled to the movable portion and configured to drive the movable portion,
wherein the holding space has an airflow passage including the first opening and the second opening, and
the movable portions close the first opening and the second opening in a steady state and open the first opening and the second opening when the holding space is opened.

REFERENCE SIGNS LIST

100 Fragrance providing device
101, 301, 401, 501 Perfume cartridge (Perfume holding member)
102, 402 Open/close mechanical part
103 Body part
111, 302, 511 First case
112, 303, 512 Second case
113 Sleeve case
114 Open/close mechanical bottom
115 Open/close mechanical fixing part
116 Stand
201, 521 Discharge hole
202, 312, 522 First opening
203, 523 First O ring
204 Shaft upper portion
205 First spring
206 Second spring
207, 317 Tolerance absorbing portion
208, 524 Perfume holder
209, 519 Perfume holding space
210, 320 Shaft lower portion
211, 321, 525 Second opening
212 Second O ring
213 Screw
221 Operation sleeve
222 Magnet fixing portion
223 Bias spring
224 Magnet
225 Operation space
226 Air intake
403 Sealing portion
404, 514 Protruding portion
405, 515 Protrusion fixing groove 406 Protrusion moving groove
513 Shaft portion
516 First raised portion
517 Second raised portion

The invention claimed is:

1. A perfume holding member comprising:
a perfume holder that holds perfume;
a holding space where the perfume holder is disposed;
a first opening and a second opening that open the holding space to outside;
movable portions that move so as to open and close the first opening and the second opening; and
a tolerance absorbing portion that absorbs a tolerance between a first opening/closing position of the first opening of a movable portion and a second opening/closing position of the second opening of the movable portion,
wherein the holding space has an airflow passage including the first opening and the second opening, and
the movable portions close the first opening and the second opening in a steady state and open the first opening and the second opening when the holding space is opened; and
wherein the movable portion has a first raised portion that closes the first opening and a second raised portion that closes the second opening.

2. The perfume holding member according to claim 1, wherein the movable portion has an attached/detached portion that is attachable or detachable by a driving source and/or magnetic means.

3. The perfume holding member according to claim 1, wherein the movable portion has an elastic body urged in a closing direction of the first opening and the second opening.

4. The perfume holding member according to claim 1, wherein the tolerance absorbing portion has an elastic body that absorbs the tolerance.

5. The perfume holding member according to claim 1, wherein the movable portion is a linear-motion mechanism that linearly moves in an opening/closing direction of the first opening and the second opening.

6. The perfume holding member according to claim 1, further comprising a lock mechanism that closes the holding space in a steady state and opens the holding space upon attachment to an external device.

7. The perfume holding member according to claim 1, further comprising a first case that includes the holding space and the first opening and a second case that is attached to the first case and includes the second opening,
wherein a sealing structure is formed at a fitting portion between the first case and the second case.

8. The perfume holding member according to claim 7, wherein the sealing structure is an O ring.

9. The perfume holding member according to claim 7, wherein the fitting portion between the first case and the second case is made of an oil seal material and/or an elastic material.

10. The perfume holding member according to claim 1, wherein the perfume holding member has a surface composed of a material selected from the group consisting of resin with low gas permeability, an organic polymer, an organic low molecule, an organic metal, a metal, and a metal film, or a combination thereof.

11. The perfume holding member according to claim 1, wherein the perfume holding member has an inner wall made of a metal.

12. The perfume holding member according to claim 1, wherein the perfume holding member is a perfume cartridge attached to a fragrance providing device.

13. A fragrance providing device comprising a perfume holding member and a driving mechanism part,
the perfume holding member including;
a perfume holder that holds perfume;
a holding space where the perfume holder is disposed;
a first opening and a second opening that open the holding space to outside;
movable portions that move so as to open and close the first opening and the second opening; and
a tolerance absorbing portion that absorbs a tolerance between a first opening/closing position of the first opening of the movable portion and a second opening/closing position of the second opening of the movable portion,
the driving mechanism part being coupled to the movable portion and configured to drive the movable portion,
wherein the holding space has an airflow passage including the first opening and the second opening, and
the movable portions close the first opening and the second opening in a steady state and open the first opening and the second opening when the holding space is opened.

* * * * *